(12) United States Patent
Chen

(10) Patent No.: US 8,809,813 B1
(45) Date of Patent: Aug. 19, 2014

(54) SCANNED UV-LED EXPOSURE DEVICE

(71) Applicant: National Central University, Taoyuan County (TW)

(72) Inventor: Chi-Feng Chen, Taoyuan County (TW)

(73) Assignee: National Central University, Taoyuan County (TW)

( * ) Notice: Subject to any disclaimer, the term of this patent is extended or adjusted under 35 U.S.C. 154(b) by 0 days.

(21) Appl. No.: 13/934,511

(22) Filed: Jul. 3, 2013

(51) Int. Cl.
*G21K 5/04* (2006.01)

(52) U.S. Cl.
USPC .................. 250/492.1; 250/493.1; 250/504 R

(58) Field of Classification Search
USPC ........ 250/492.1, 492.2, 492.22, 493.1, 503.1, 250/504 R
See application file for complete search history.

(56) References Cited

U.S. PATENT DOCUMENTS

| | | | |
|---|---|---|---|
| 2008/0280227 A1* | 11/2008 | Sievers | 430/270.1 |
| 2010/0242299 A1* | 9/2010 | Siegel | 34/275 |
| 2011/0134199 A1* | 6/2011 | Noro et al. | 347/102 |

* cited by examiner

*Primary Examiner* — Nicole Ippolito
(74) *Attorney, Agent, or Firm* — Jackson IPG PLLC

(57) ABSTRACT

A scanned ultraviolet-light emitting diode (UV-LED) exposure device, exposing a large area by using a periodic UV-LED exposure light source with a fixed rate in an exposure task without a need of stopping movement of the device, so as to periodically repeat a use of an exposure light source to increase a use efficiency of the energy source, resulting in an improved uniformity of exposure, with the LEDs alternatively arranged policy, which further results in an improved yield. In addition, the overall design of the upper and lower exposure stations and the periodic moving ring assembly sufficiently employs the available space, and results in a reduced volume, a corresponding production space, energy consumption and production cost.

16 Claims, 3 Drawing Sheets

SCANNED UV-LED EXPOSURE DEVICE

FIELD OF THE INVENTION

The present invention is related to a scanned ultraviolet-light emitting diode (UV-LED) exposure device, and particularly to an LED exposure device having a large area and separated portions based exposure capability, and more particularly to a scanned UV-LED exposure device performing a scanned exposure task on the large object area based on a periodic manner by a fixed rate without a need of stopping movement of the device, so as to periodically repeat a use of an exposure light source to increase a use efficiency of the energy source, resulting in an improved uniformity of exposure.

DESCRIPTION OF THE RELATED ART

In the past, an exposure station other than the ultraviolet-light emitting diode (UV-LED) system is quite space consuming, and so is a manufacturing assembly space involved with that. In the currently available UV-based exposure station, an exposure light source exposes an object exposure area in a separated manner in the case that the exposure station is used without special improvement. When the light source moves along different separated portions, it has to repeat the actions between moving and stopping. This results in an irregular scan speed and thus an unstable UV light source for the separated portions. Further, this exposure manner with respect to a single LED position may cause an insufficient radiant illumination and thus an unsatisfactory exposure uniformity, leading also to a low yield.

In addition, in such exposure task regime, the light source has to be kept being turned on, which results in a short UV light source lifetime. Further, the light source has to be warmed in a preparation stage whenever the UV light source is turned on to use, making the light source hard to be controlled in its on/off states.

In view of the above problems of the insufficient exposure uniformity of the light source on the different portions of the object exposure area and the use efficiency of the light source energy, there is a need to provide an exposure means effectively improving the prior art.

SUMMARY OF THE INVENTION

It is, therefore, an object of the present invention to provide a scanned ultraviolet-light emitting diode (UV-LED) exposure device, which can effectively overcome the problems encountered in the prior art, having a large area and separated portions based exposure capability and performing a scanned exposure task on the large object area based on a periodic manner by a fixed rate without a need of stopping movement of the device, so as to periodically repeat a use of an exposure light source to increase a use efficiency of the energy source, resulting in an improved uniformity of exposure.

It is a secondary object of the present invention to provide a scanned UV-LED exposure device having a reduced volume, corresponding production space, energy consumption and production cost, and an improved production efficiency.

To achieve the above objects, the scanned UV-LED exposure device according to the present invention comprises an exposure unit, comprising a set of upper exposure station and a lower exposure station having a distance therebetween, the upper exposure station having a lower surface and the lower exposure station having an upper surface, each of the lower and upper surfaces having a substrate coated with a resist layer composed of a photo-sensitive material thereon, and the respective substrate of the upper and lower exposure stations being taken as a linear object exposure area having a vertical direction; a UV-LED illumination unit, being a 2-D matrix composed of a plurality of LEDs lying on a plurality of stripes, each of the stripes having a designated number of LEDs, respectively, having a horizontal direction and a vertical direction and arranged in parallel, being separated from each other for each pair of adjacent ones thereamong, having one of the designated number of LEDs in the horizontal direction thereof and having the vertical direction in perpendicular with the vertical direction of the linear object exposure area; and a periodic moving ring assembly, arranged on a center position between the upper and lower exposure stations in the exposure unit, having a first end, a second end, an inner circumference and an outer circumference having the plurality of UV-LED stripes thereon, wherein the periodic moving ring assembly continuously moves in an exposure task in a fixed rate, so as to expose the linear object exposure area of the upper and lower exposure stations.

In an embodiment, the periodic moving ring assembly comprises an active wheel, arranged at the first end of the periodic moving ring assembly to drive the periodic moving ring assembly to rotate; a passive wheel group, arranged within the inner circumference of the periodic moving ring assembly and comprising a plurality of passive wheels to bear the periodic moving ring assembly, the plurality of stripes and the plurality of LEDs to assist in a smooth rotation of the periodic moving ring assembly; a guiding wheel, arranged on the second end opposed to the first end of the periodic moving ring assembly to assist in the smooth rotation of the periodic moving ring assembly; and an active heat sinking element, arranged within the periodic moving ring assembly to actively heat sink the periodic moving ring assembly.

In an embodiment, the periodic moving ring assembly is a double-layered structure formed of the active wheel and the guiding wheel and moving in a horizontal direction.

In an embodiment, adjacent ones of the plurality of passive wheels are arranged with a distance to each other and the passive wheel group has a distance from the active wheel and the guiding wheel in the periodic moving ring assembly.

In an embodiment, the active heat sinking element includes a water-cooled element and an air-cooled element.

In an embodiment, the LED has a secondary optical element and an LED light source.

In an embodiment, the secondary optical element includes a lens and a reflector.

In an embodiment, each of the plurality of stripes includes a lens stripe and a reflector stripe.

In an embodiment, the LED matrix further has a diffusing plate thereabove totally covering the plurality of LEDs.

In an embodiment, the diffusing plate is an entire sheet structure.

In an embodiment, the diffusing plate is a rib structure.

In an embodiment, the diffusing plate is a structure having a plurality of stripes.

In an embodiment, the diffusing plate is made of a UV-transparent material and includes quartz and glass.

In an embodiment, when the periodic moving ring assembly rotates upward and downward at the first and second ends, respectively, the ones of the plurality of LEDs at the first and second ends are further each controlled as being turned off, respectively.

In an embodiment, each of the plurality of stripes is arranged in the vertical direction thereof in parallel with the vertical direction of the linear object exposure area.

In an embodiment, the designated number of LEDs in the adjacent ones of the plurality of stripes are alternatively arranged to each other, respectively.

BRIEF DESCRIPTIONS OF THE DRAWINGS

The present invention will be better understood from the following detailed descriptions of the preferred embodiments according to the present invention, taken in conjunction with the accompanying drawings, in which.

DESCRIPTION OF THE PREFERRED EMBODIMENTS

Figure 1:
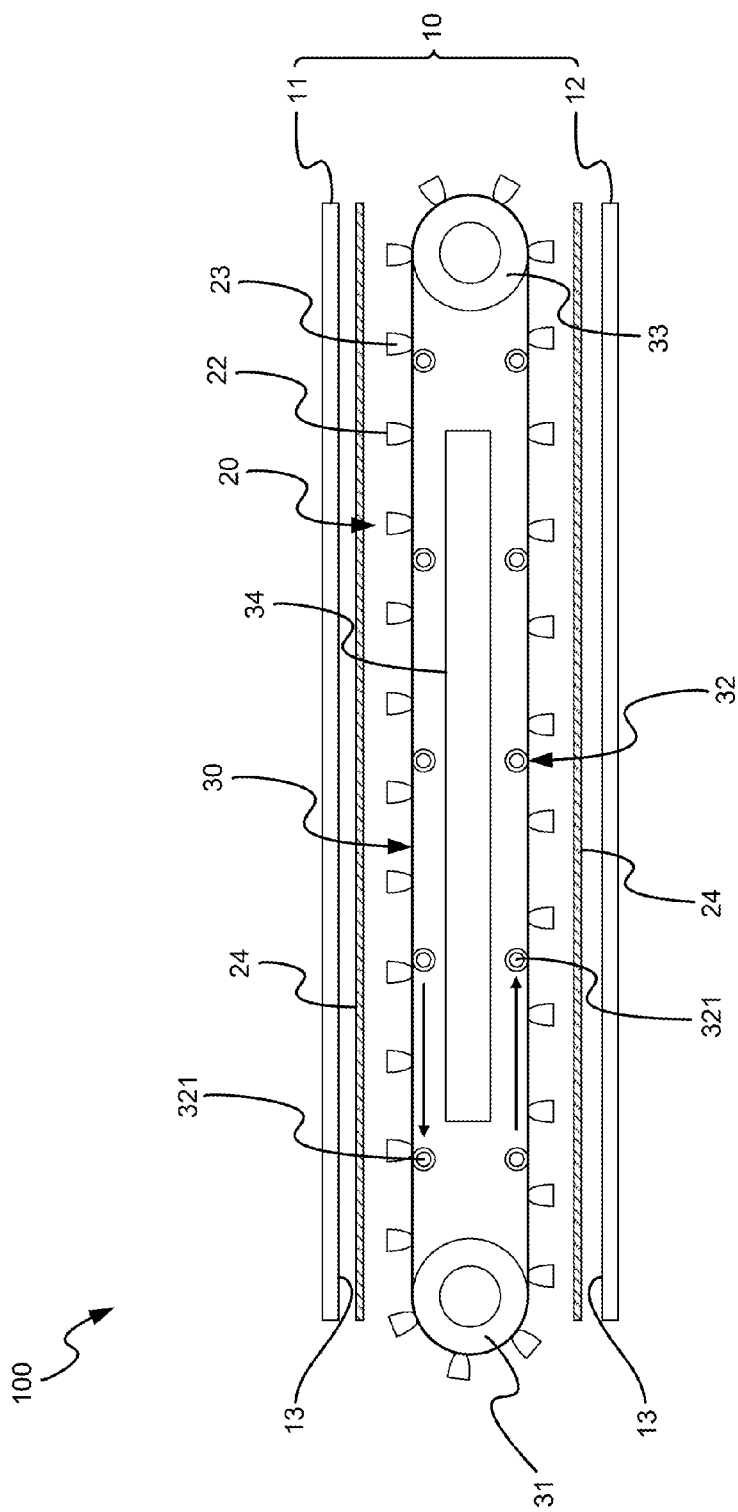
FIG. 1 is a schematic diagram of a structure of a scanned ultraviolet-light emitting diode (UV-LED) exposure device according to the present invention.
Figure 2:
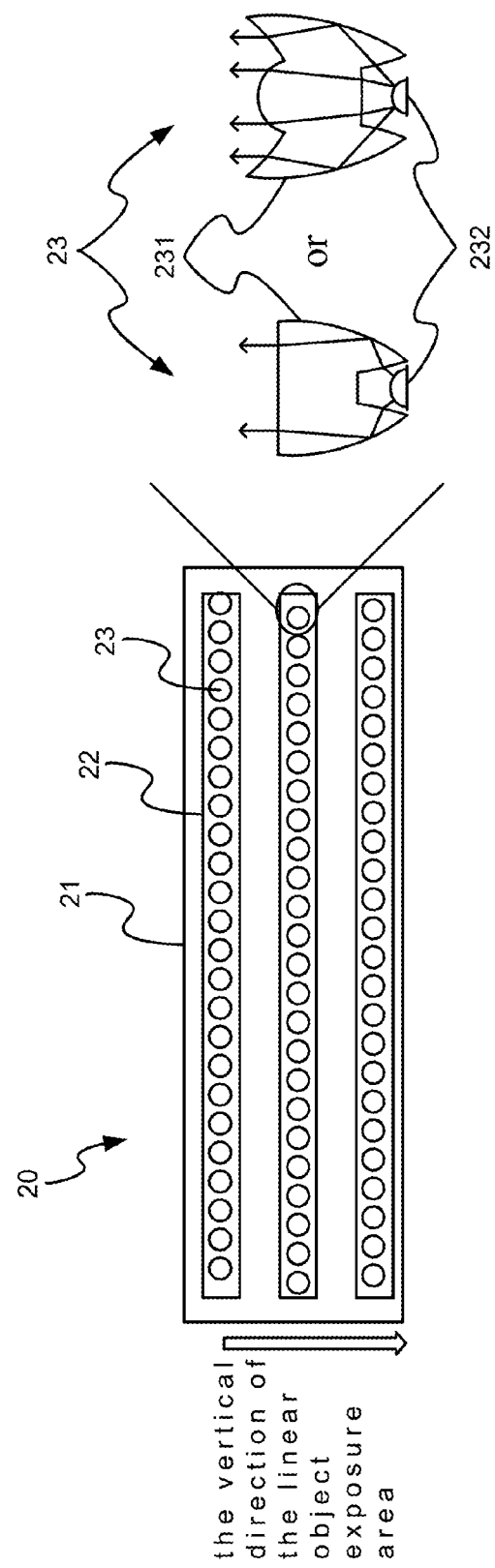
FIG. 2 is a vertical view of a UV-LED illumination unit according to a preferred embodiment of the present invention.
Figure 3:
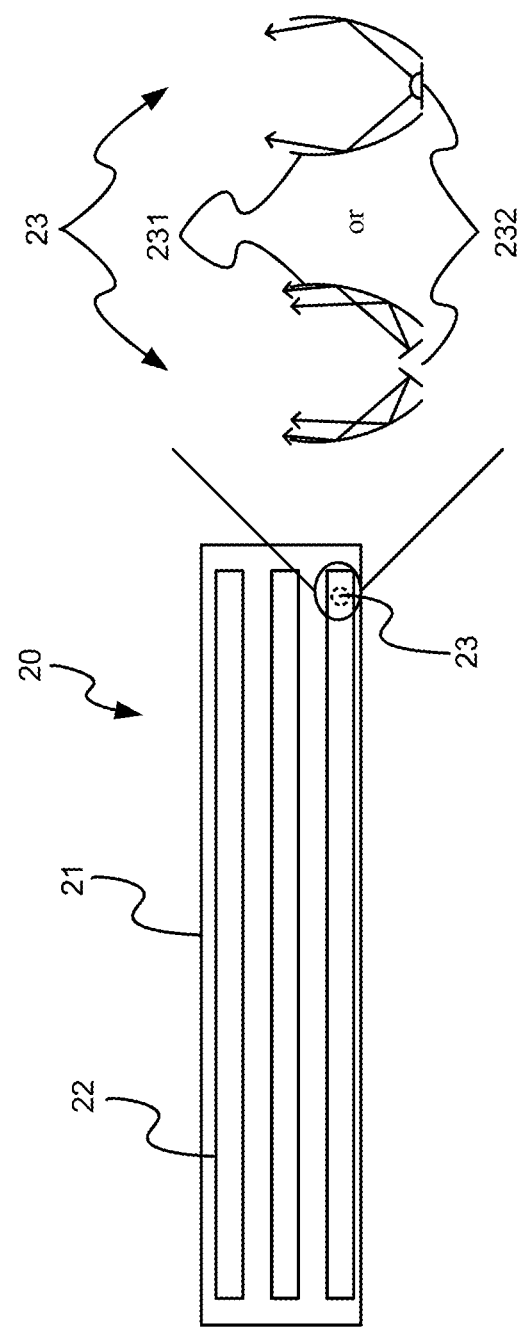
FIG. 3 is a vertical view of the UV-LED illumination unit according to another preferred embodiment of the present invention.

Referring assembly to FIG. 1 through FIG. 3, a schematic diagram of a structure of a scanned ultraviolet-light emitting diode (UV-LED) exposure device, a vertical view of a UV-LED illumination unit in a preferred embodiment and a vertical view of the UV-LED illumination unit in another preferred embodiment according to the present invention are shown, respectively.

As shown, the scanned UV-LED exposure device of the present invention is an LED exposure station having a large area and separated portions exposure capability, where a light source for exposure goes through a mask to illuminate an object exposure area.

The scanned UV-LED exposure device 100 comprises an exposure unit 10, a UV-LED illumination unit 20, and a periodic moving ring assembly 30, The exposure unit 10 comprises a set of upper exposure station 11 and a lower exposure station 12, which are arranged with a distance therebetween. Each of the upper and lower exposure stations 11, 12 has a surface, the two surfaces facing each other. The two surfaces each have a substrate coated with a resist layer composed of a photo-sensitive material thereon. The respective substrate of the upper and lower exposure stations is taken as a linear object exposure area 13.

The UV-LED illumination unit 20 is a 2-D matrix composed of a plurality of LEDs 21, which are averagely laid on a plurality of stripes 22. Specifically, a designated number of LEDs 23 out of the plurality of LEDs 21 are arranged on one such strip 22, respectively. These stripes are arranged in parallel and separated from each other for the adjacent ones among the total stripes 22. Each of the plurality of stripes 22 has only one of the designated number of LEDs. Each of the stripes 22 has its vertical direction in perpendicular with a vertical direction of the linear object exposure area 13 on the upper and lower exposure stations 11, 12, respectively.

The periodic moving ring assembly 30 is arranged on a center position between the upper and lower exposure stations 11, in the exposure unit 10. The plurality of UV-LED stripes 22 are arranged on an outer circumference of the periodic moving ring assembly 30.

The stripes 22 are arranged in parallel to the vertical direction of the linear object exposure area 13 in their vertical directions, respectively. Further, the LEDs in the adjacent ones of the plurality of stripes 22 are alternatively arranged to each other respectively, as shown in FIG. 2, to effectively accumulate the radiated energy of the LEDs 23 on the total stripes 22.

Each of the plurality of LEDs 23 is composed of a secondary optic element 231 and an LED light source 232. In the case that the secondary optic element 231 is a lens, the stripe 22 is a lens stripe, as shown in FIG. 2. On the other hand, when the secondary optic element 231 is a reflector, the stripe 22 is a reflector stripe, as shown in FIG. 3.

The periodic moving ring assembly 30 is a double-layered structure formed of the active wheel 31 and the guiding wheel 33. The active wheel 31 is arranged at an end of the periodic moving ring assembly 30 to drive the periodic moving ring assembly 30 to rotate. The passive wheel group 32 is composed of a plurality of passive wheels 321 and arranged within an inner circumference of the periodic moving ring assembly 30. The passive wheel group 32 is arranged between the active wheel 31 and the guiding wheel 33 to bear the periodic moving ring assembly 30 and assist in a smooth rotation of the periodic moving ring assembly 30.

The guiding wheel 33 is arranged on the other end, opposed to the end with the active wheel 31, of the periodic moving ring assembly 30 to assist in the smooth rotation of the periodic moving ring assembly 30.

The active heat sinking element 34 is arranged within the periodic moving ring assembly 30 to actively heat sink the periodic moving ring assembly 30. The active heat sinking element 34 may be a water-cooled element or an air-cooled element.

The LED matrix light source 21 further has a diffusing plate 24 arranged above and the diffusing plate 24 totally covers the plurality of LEDs 23. The diffusing plate 24 is made of a UV-transparent material and may be quartz or glass.

In a preferred embodiment, the diffusing plate 24 is an entire sheet structure. In another preferred embodiment, the diffusing plate 24 is a rib structure. In yet another preferred embodiment, the diffusing plate 24 is a structure having a plurality of stripes. In this manner, the novel scanned UV-LED exposure device 100 is formed.

In operation, the periodic moving ring assembly 30 continuously rotates without a need of stopping movement in an exposure task. This rotation is mainly driven by the active wheel 31, along with the assistance of the guiding wheel 33, with a fixed rate. In such manner, the LED matrix light source 21 is also caused to rotate. As such, the light source 21 may expose with respect to the linear object area 13 of the upper and lower exposure stations 11, 12, respectively.

In addition, when the periodic moving ring assembly 30 rotates upward and downward at the two ends, the ones of the plurality of LEDs 23 at the first and second ends may be each further controlled as being turned off. In this manner, the LED matrix light source may have a lengthened lifetime, and thus achieve in an efficacy of reduced energy consumption.

In view of the above, the scanned UV-LED exposure device of the present invention exposes a large area by using a periodic UV-LED exposure light source with a fixed rate in an exposure task without a need of stopping movement of the device, so as to periodically repeat a use of an exposure light source to increase a use efficiency of the energy source, resulting in an improved uniformity of exposure, with the LEDs alternatively arranged policy, which further results in an improved yield.

In addition, the overall design of the upper and lower exposure stations and the periodic moving ring assembly sufficiently employs the available space, and results in a reduced volume, a corresponding production space, energy consumption and production cost.

In view of the above, the scanned UV-LED exposure device according to the present invention can effectively overcome the problems encountered in the prior art by having a large area and separated portions based exposure capability, and performing a scanned exposure task on the large object area based on a periodic manner by a fixed rate without a need of stopping movement of the device, so as to periodically repeat a use of an exposure light source to increase a use efficiency of the energy source, resulting in an improved uniformity of exposure.

Therefore, the present invention can be deemed as more practical, improved and necessary to users, compared with the prior art.

The above described is merely examples and preferred embodiments of the present invention, and not exemplified to intend to limit the present invention. Any modifications and changes without departing from the scope of the spirit of the present invention are deemed as within the scope of the present invention. The scope of the present invention is to be interpreted with the scope as defined in the claims.

The invention claimed is:

1. A scanned ultraviolet-light emitting diode (UV-LED) exposure device, comprising:
    a set of upper exposure station and a lower exposure station having a distance therebetween, the upper exposure station having a lower surface and the lower exposure station having an upper surface, each of the lower and upper surfaces having a substrate coated with a resist layer composed of a photo-sensitive material thereon, and the respective substrate of the upper and lower exposure stations being taken as a linear object exposure area having a vertical direction;
    a UV-LED illumination unit, being a 2-D matrix composed of a plurality of LEDs lying on a plurality of stripes, each of the stripes having a designated number of LEDs, respectively, having a horizontal direction and a vertical direction and arranged in parallel, being separated from each other for each pair of adjacent ones thereamong, having one of the designated number of LEDs in the horizontal direction thereof and having the vertical direction in perpendicular with the vertical direction of the linear object exposure area; and
    a periodic moving ring assembly, arranged on a center position between the upper and lower exposure stations in the exposure unit, having a first end, a second end, an inner circumference and an outer circumference having the plurality of UV-LED stripes thereon,
    wherein the periodic moving ring assembly continuously moves in an exposure task in a fixed rate, so as to expose the linear object exposure area of the upper and lower exposure stations.

2. The device according to claim 1, wherein the periodic moving ring assembly comprises:
    an active wheel, arranged at the first end of the periodic moving ring assembly to drive the periodic moving ring assembly to rotate;
    a passive wheel group, arranged within the inner circumference of the periodic moving ring assembly and comprising a plurality of passive wheels to bear the periodic moving ring assembly, the plurality of stripes and the plurality of LEDs to assist in a smooth rotation of the periodic moving ring assembly;
    a guiding wheel, arranged on the second end opposed to the first end of the periodic moving ring assembly to assist in the smooth rotation of the periodic moving ring assembly; and
    an active heat sinking element, arranged within the periodic moving ring assembly to actively heat sink the periodic moving ring assembly.

3. The device according to claim 2, wherein the periodic moving ring assembly is a double-layered structure formed of the active wheel and the guiding wheel and moving in a horizontal direction.

4. The device according to claim 2, wherein adjacent ones of the plurality of passive wheels are arranged with a distance to each other and the passive wheel group has a distance from the active wheel and the guiding wheel in the periodic moving ring assembly.

5. The device according to claim 2, wherein the active heat sinking element includes a water-cooled element and an air-cooled element.

6. The device according to claim 1, wherein the LED has a secondary optical element and an LED light source.

7. The device according to claim 6, wherein the secondary optical element includes a lens and a reflector.

8. The device according to claim 1, wherein each of the plurality of stripes includes a lens stripe and a reflector stripe.

9. The device according to claim 1, wherein the LED matrix further has a diffusing plate thereabove totally covering the plurality of LEDs.

10. The device according to claim 9, wherein the diffusing plate is an entire sheet structure.

11. The device according to claim 9, wherein the diffusing plate is a rib structure.

12. The device according to claim 9, wherein the diffusing plate is a structure having a plurality of stripes.

13. The device according to claim 9, wherein the diffusing plate is made of a UV-transparent material and includes quartz and glass.

14. The device according to claim 1, wherein when the periodic moving ring assembly rotates upward and downward at the first and second ends, respectively, the ones of the plurality of LEDs at the first and second ends are further each controlled as being turned off, respectively.

15. The device according to claim 1, wherein each of the plurality of stripes is arranged in the vertical direction thereof in parallel with the vertical direction of the linear object exposure area.

16. The device according to claim 1, wherein the designated number of LEDs in the adjacent ones of the plurality of stripes are alternatively arranged to each other, respectively.

* * * * *